United States Patent
Thomas et al.

(10) Patent No.: US 10,179,004 B2
(45) Date of Patent: Jan. 15, 2019

(54) METHOD OF AMPUTATING AND MORCELLATING A UTERUS

(71) Applicant: GYRUS MEDICAL LIMITED, Cardiff (GB)

(72) Inventors: Daniel John Thomas, Cardiff (GB); Neill Tomas Brennan, Newport (GB)

(73) Assignee: GYRUS MEDICAL LIMITED, Cardiff (GB)

( * ) Notice: Subject to any disclaimer, the term of this patent is extended or adjusted under 35 U.S.C. 154(b) by 713 days.

(21) Appl. No.: 14/921,016

(22) Filed: Oct. 23, 2015

(65) Prior Publication Data
US 2016/0113679 A1 Apr. 28, 2016

Related U.S. Application Data

(60) Provisional application No. 62/069,552, filed on Oct. 28, 2014.

(51) Int. Cl.
| | |
|---|---|
| *A61B 18/14* | (2006.01) |
| *A61B 17/3205* | (2006.01) |
| *A61B 17/00* | (2006.01) |
| *A61B 17/42* | (2006.01) |
| *A61B 17/32* | (2006.01) |
| *A61B 18/00* | (2006.01) |

(52) U.S. Cl.
CPC .... *A61B 17/32056* (2013.01); *A61B 18/1485* (2013.01); *A61B 2017/00287* (2013.01); *A61B 2017/320024* (2013.01); *A61B 2017/4216* (2013.01); *A61B 2018/00559* (2013.01); *A61B 2018/00601* (2013.01); *A61B 2018/141* (2013.01)

(58) Field of Classification Search
CPC ........ A61B 2018/141; A61B 2018/142; A61B 2018/1422; A61B 2017/00287; A61B 2017/4216; A61B 17/221; A61B 17/48
See application file for complete search history.

(56) References Cited

U.S. PATENT DOCUMENTS

| | | | |
|---|---|---|---|
| 5,037,379 A | 8/1991 | Clayman | |
| 5,647,372 A | 7/1997 | Tovey et al. | |
| 8,137,372 B2 * | 3/2012 | Kondoh | A61B 17/32056 606/170 |
| 2010/0219091 A1 * | 9/2010 | Turner | A61B 17/00234 206/438 |

* cited by examiner

*Primary Examiner* — Ronald Hupczey, Jr.
*Assistant Examiner* — Bo Ouyang
(74) *Attorney, Agent, or Firm* — Oliff PLC

(57) ABSTRACT

A method of amputating and morcellating a uterus (10) includes introducing a first tissue bag (1) into the abdomen of the patient, and placing the first tissue bag over the uterus. A laparoscopic surgical instrument (11) is introduced into the first tissue bag, and the uterus (10) is amputated using the laparoscopic surgical instrument. The first tissue bag (1) is closed around the amputated uterus, and the first tissue bag containing the amputated uterus is placed into a second tissue bag (20). A morcellating instrument is introduced into the second tissue bag (20) and the uterus is morcellated within the second tissue bag. Once the uterus (10) has been morcellated, the second tissue bag (20) containing the morcellated uterus is removed from the abdomen of the patient.

20 Claims, 3 Drawing Sheets

METHOD OF AMPUTATING AND MORCELLATING A UTERUS

This application claims the benefit of U.S. Provisional Application No. 62/069,552 filed 28 Oct. 2014, the entire contents of which are incorporated herein by reference.

This invention relates to a method for amputating and morcellating a female uterus. Due to the perceived risks associated with the "seeding" of cancerous tissue, the morcellation of tissue is often carried out in a tissue bag surrounding or containing the tissue. An example of such a tissue bag is given in U.S. Pat. No. 5,037,379. The present invention attempts to provide an improvement to methods such as these.

BRIEF DESCRIPTION OF THE INVENTION

Accordingly, a method of amputating and morcellating a uterus is provided, comprising the steps of
 (i) introducing a first tissue bag into the abdomen of the patient,
 (ii) placing the first tissue bag over the uterus,
 (iii) introducing a laparoscopic surgical instrument into the first tissue bag,
 (iv) amputating the uterus using the laparoscopic surgical instrument,
 (v) closing the first tissue bag around the amputated uterus,
 (vi) placing the first tissue bag containing the amputated uterus into a second tissue bag,
 (vii) introducing a morcellating instrument into the second tissue bag,
 (vii) morcellating the uterus within the second tissue bag, and
 (viii) removing the second tissue bag containing the morcellated uterus from the abdomen of the patient.

By using not one but two tissue bags, the tissue is constrained not only when being morcellated but also when the amputation of the uterus from the cervix is being performed. In this way, the seeding of tissue is minimised, not only during morcellation but also during the separation of the uterus from the surrounding tissue.

Conveniently, the laparoscopic surgical instrument is a snare device, typically an electrosurgical snare. Preferably, the step of introducing the snare or other laparoscopic instrument into the first tissue bag comprises introducing the instrument through an aperture in the side of the first tissue bag. This additional aperture for receiving the laparoscopic instrument means that the instrument does not have to be maneuvered through the main opening of the first tissue bag, with the result that the first tissue bag can contain the uterus more effectively during the amputation of the uterus from the surrounding tissue. Conventional tissue bags have a single opening, either such that the tissue bag can be placed over a tissue structure, or such that tissue may be dissected and placed into the bag. However, even if the tissue bag is placed over a large tissue structure, the single opening means that the tissue structure must be resected from surrounding tissue with the resection instrument entering the tissue bag trough the opening. This means that the bag must be at least partially open while such resection is taking place, allowing for a potential lack of containment during tissue resection. In contrast, by using a different opening for the introduction of surgical instruments, the containment of tissue during tissue resection can be improved.

The first tissue bag conveniently has a ring of semi-rigid material running around the opening thereof. Preferably, the bag is elongate in structure having a major axis and a minor axis, the instrument aperture being spaced from the opening along the major axis. Typically, the instrument aperture is spaced from the opening by a distance of between 5 mm & 15 mm, typically 10 mm. The material of the first tissue bag is typically polyurethane.

Once the uterus has been amputated, the first tissue bag is placed into the second tissue bag and the uterus can be morcellated. Preferably, the morcellating instrument is an electrosurgical morcellator, as this is less likely to puncture the second tissue bag during morcellation.

In one arrangement, the step of morcellating the uterus includes removing the first tissue bag from the second tissue bag prior to morcellating the uterus. Alternatively, the step of morcellating the uterus includes morcellating the first tissue bag along with the uterus. Whether the first tissue bag is removed or morcellated along with the uterus, it has served its intended purpose in that it has contained the uterus while it was amputated from the cervix.

Whether the first tissue bag is removed or morcellated along with the uterus, the step of morcellating the uterus is facilitated by insufflating the second tissue bag. This allows for improved access to the uterus within the second tissue bag, and for better visualisation of the uterus during the morcellation thereof. Preferably, the step of morcellating the uterus includes
 (i) pulling the second tissue bag partly through the incision such that the portion of the tissue bag including the opening and the aperture is outside the patient,
 (ii) insufflating the second tissue bag with an insufflation gas, and
 (iii) morcellating the uterus within the tissue bag using the morcellating instrument.

BRIEF DESCRIPTION OF THE DRAWINGS

The invention will now be further described, by way of example only, with reference to the accompanying drawings, in which.

DETAILED DESCRIPTION OF THE INVENTION

Figure 1:
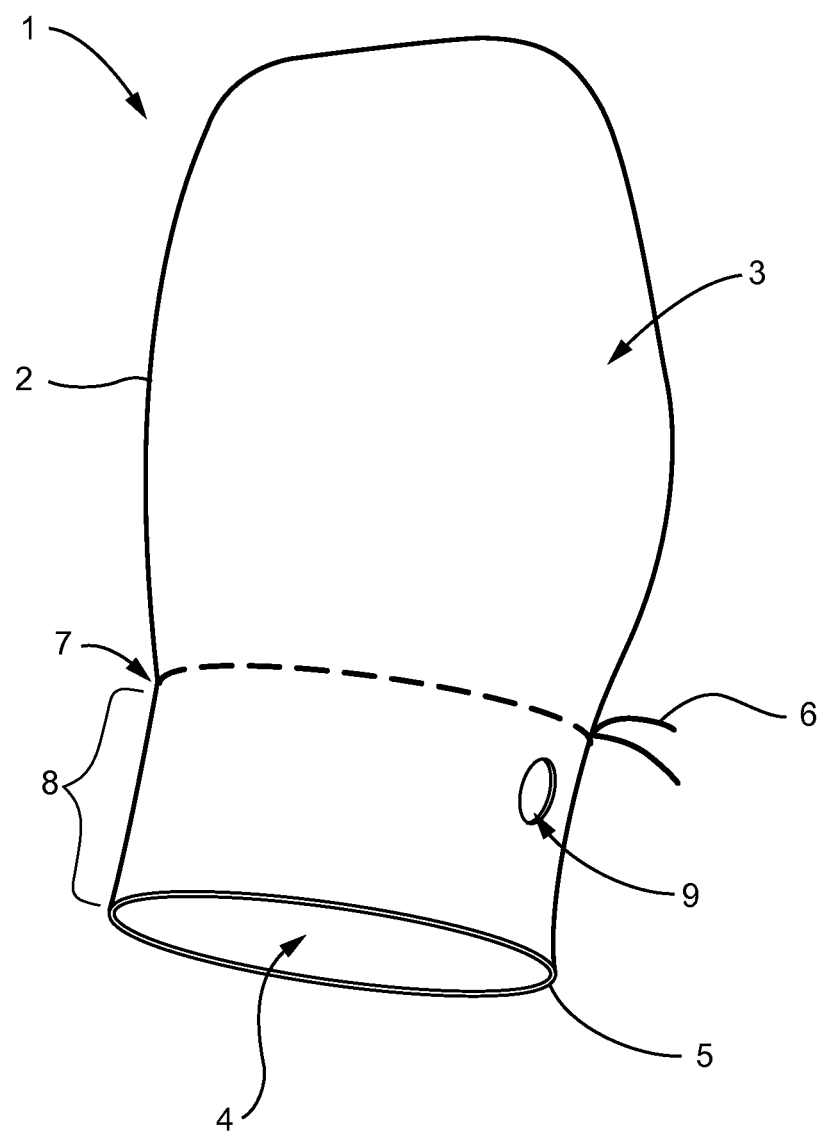
FIG. 1 is a schematic side view of a first tissue bag used in a method in accordance with the present invention.

Referring to FIG. 1, a polyurethane tissue bag is shown generally at 1, and includes a transparent wall 2 forming an internal enclosure 3 with an opening 4 allowing access to the enclosure 3. Around the opening 4 is a semi-rigid ring 5 which ensures that the bag 1 assumes its expanded shape once it has been deployed within the body of a patient. A drawstring 6 is located on the wall 2 at a position 7 spaced from the opening 4 so as to define an interim portion of the bag, hereby designated the neck portion 8. Within the neck portion 8 is an instrument aperture 9, located between the opening 4 and the drawstring 6.

Figure 2:
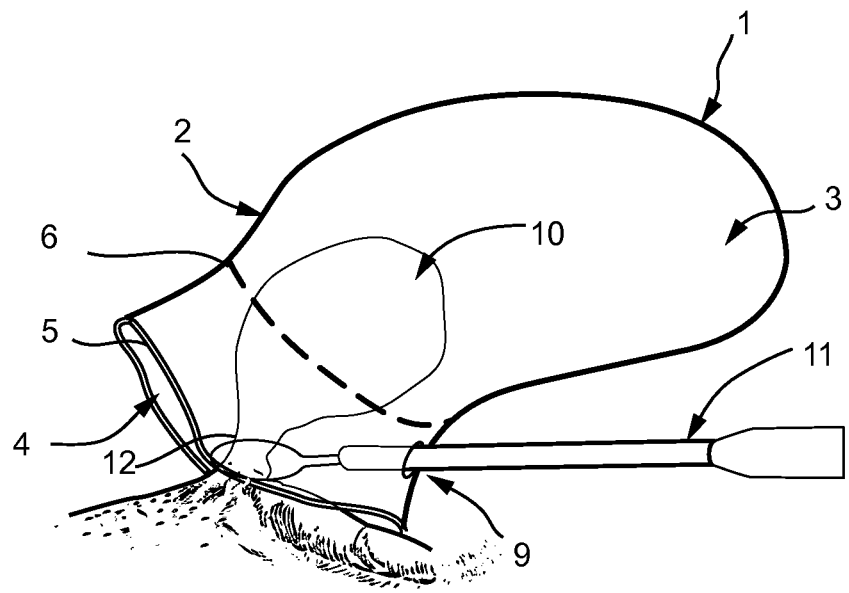
FIG. 2 is a schematic side view showing the tissue bag of FIG. 1 being placed over a female uterus.

In use the tissue bag 1 is introduced into the body of a patient, and allowed to expand, with the semi-rigid ring 5 assisting in allowing the bag to obtain its deployed shape. In one arrangement, shown in FIG. 2, the tissue bag 1 is placed over the uterus 10 of a female patient, with the uterus 10 being received within the enclosure 3. A laparoscopic surgical instrument in the form of a snare device 11 is introduced through the instrument aperture 9, so as to be in the region of the cervix 12.

Figure 3:
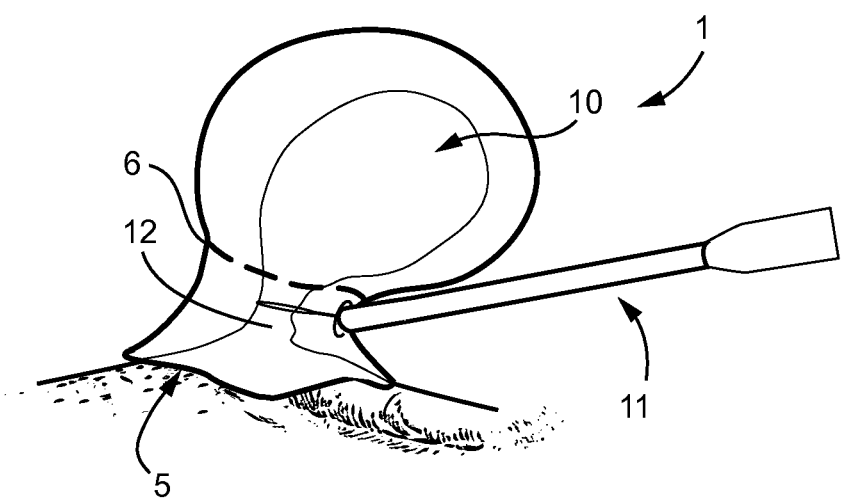
FIG. 3 is a schematic side view showing the uterus of FIG. 2 being amputated within the tissue bag.

Once in position, the drawstring 6 is pulled (by a grasping laparoscopic instrument, not shown) in order to locate the tissue bag more firmly around the uterus 10. This is the position shown in FIG. 3. The snare device 11 is then used to separate the uterus 10 from the cervix 12. The tissue bag 1, being located around the uterus 10 and over the cervix 12 at this point in the procedure, helps to ensure that any tissue fragments produced as the uterus is amputated do not spread around the body of the patient.

Figure 4:
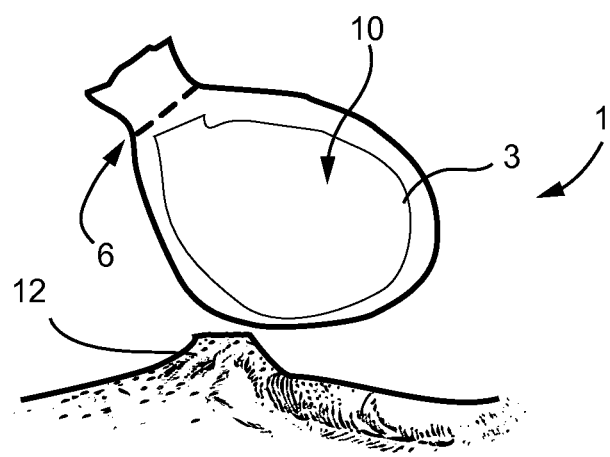
FIG. 4 is a schematic side view showing the amputated uterus within the first tissue bag of FIG. 1.
Figure 5:
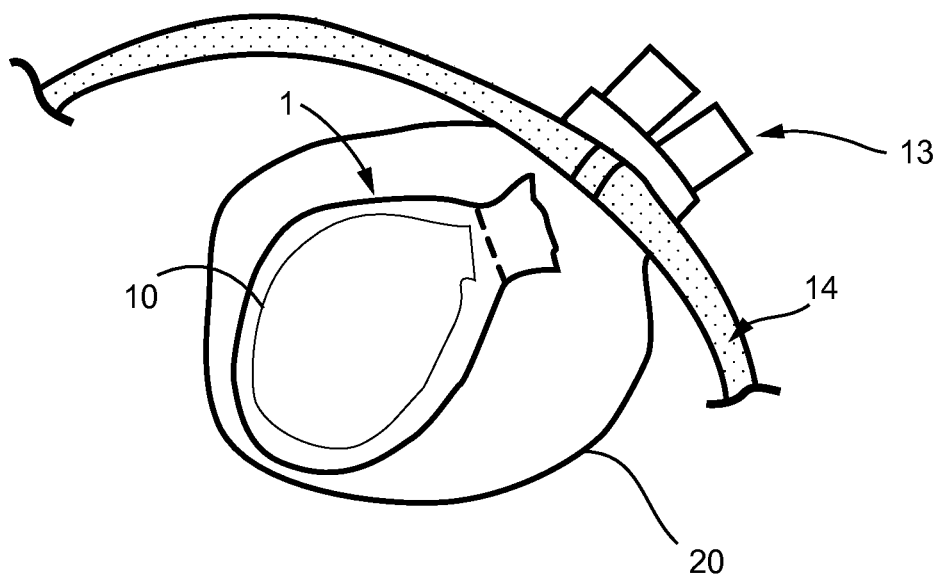
FIG. 5 is a schematic side view showing the first tissue bag within a second tissue bag ready for morcellation of the uterus in accordance with the method of the present invention.

Once the uterus 10 has been separated from the cervix 12, the drawstring 6 is fully tightened to contain the amputated uterus within the enclosure 3, as shown in FIG. 4. The tissue bag 1 is then manipulated and placed into a second tissue bag 20, which is then attached to a port 13 located at the surface 14 of the patient's body. Once the second tissue bag 20 is attached to the port 13, it is expanded by insufflating it, and then a tissue morcellator (not shown) is used to morcellate the uterus 10 (together with the first tissue bag 1) into small pieces. Once the uterus 10 and bag 1 have been morcellated into small pieces, they can be removed through the port 13 from the patient's body.

Alternatively, once the second tissue bag 20 has been attached to the port 13, and insufflation applied to expand the second tissue bag 20, the first tissue bag 1 can be manipulated and removed through the port 13. After the first tissue bag 1 has been removed, the uterus 10 can be morcellated into small pieces as previously described. The small pieces can be removed from the second tissue bag 20 through the port 13 as they are created. Alternatively, the uterus can be morcellated into small pieces and the pieces can be left in the second tissue bag 20 until all of the uterus has been morcellated in this way. Once the uterus 10 is entirely in small pieces, the second tissue bag 20, containing the small pieces of uterus, can be removed through the port 13 from the patient's body.

What is claimed is:

1. A method of amputating and morcellating a uterus of a patient, the method comprising:
   (i) introducing a first tissue bag into the abdomen of the patient,
   (ii) placing the first tissue bag over the uterus,
   (iii) introducing a laparoscopic surgical instrument into the first tissue bag,
   (iv) amputating the uterus using the laparoscopic surgical instrument,
   (v) closing the first tissue bag around the amputated uterus,
   (vi) placing the first tissue bag containing the amputated uterus into a second tissue bag,
   (vii) introducing a morcellating instrument into the second tissue bag,
   (vii) morcellating the uterus within the second tissue bag, and
   (viii) removing the second tissue bag containing the morcellated uterus from the abdomen of the patient.
2. The method according to claim 1, wherein the laparoscopic surgical instrument is a snare device.
3. The method according to claim 2, wherein the snare device is an electrosurgical snare.
4. The method according to claim 1, wherein the step of introducing a laparoscopic instrument into the first tissue bag comprises introducing the instrument through an aperture in the side of the first tissue bag.
5. The method according to claim 1, wherein the morcellating instrument is an electrosurgical morcellator.
6. The method according to claim 1, wherein the morcellating of the uterus includes removing the first tissue bag from the second tissue bag prior to morcellating the uterus.
7. The method according to claim 1, wherein the morcellating of the uterus includes morcellating the first tissue bag along with the uterus.
8. The method according to claim 1, wherein the morcellating of the uterus includes insufflating the second tissue bag.
9. The method according to claim 8, wherein the morcellating of the uterus includes:
   (i) pulling the second tissue bag partly through though an incision in the patient, such that a portion of the first tissue bag including an opening for access to an internal enclosure of the tissue bag and the aperture are outside the patient,
   (ii) insufflating the second tissue bag with an insufflation gas, and
   (iii) morcellating the uterus within the second tissue bag using the morcellating instrument.
10. The method according to claim 1, wherein the first tissue bag includes an internal enclosure with an opening allowing access to the enclosure.
11. The method according to claim 10, wherein the first tissue bag further includes a semi-rigid ring around the opening to ensure that the first tissue bag assumes an expanded shape once the first tissue bag has been deployed within a body of a patient.
12. The method according to claim 10, wherein the first tissue bag includes a transparent wall forming the internal enclosure.
13. The method according to claim 12, wherein the first tissue bag further includes a drawstring that is located in the wall at a position spaced from the opening so as to define a neck portion of the first tissue bag.
14. The method according to claim 13, wherein the first tissue bag further includes an instrument aperture within the neck portion which is located between the opening and the drawstring.
15. A method of amputating and morcellating a uterus of a patient, the method comprising:
   (i) introducing a first tissue bag into an incision made in an abdomen of the patient, the first tissue bag including an internal enclosure with an opening that allows access to the enclosure,
   (ii) placing the first tissue bag over the uterus so that the uterus is located within the internal enclosure,
   (iii) introducing a laparoscopic surgical instrument into the first tissue bag through an instrument aperture located within a neck portion of the first tissue bag,
   (iv) amputating the uterus using the laparoscopic surgical instrument,
   (v) closing the first tissue bag around the amputated uterus using a drawstring located in the neck portion of the first tissue bag,
   (vi) introducing a second tissue bag into the abdomen of the patient, and placing the first tissue bag containing the amputated uterus into the second tissue bag, (vii) introducing a morcellating instrument into the second tissue bag, (vii) morcellating the uterus within the second tissue bag, and (viii) removing the second tissue bag containing the morcellated uterus from the abdomen of the patient.

16. The method according to claim 15, wherein the laparoscopic surgical instrument is a snare device.

17. The method according to claim 16, wherein the snare device is an electrosurgical snare.

18. The method according to claim 15, wherein the morcellating instrument is an electrosurgical morcellator.

19. The method according to claim 15, wherein the morcellating of the uterus includes removing the first tissue bag from the second tissue bag prior to morcellating the uterus.

20. The method according to claim 15, wherein the morcellating of the uterus includes morcellating the first tissue bag along with the uterus.

\* \* \* \* \*